US012630519B2

(12) United States Patent
Grant et al.

(10) Patent No.: US 12,630,519 B2
(45) Date of Patent: May 19, 2026

(54) METHODS AND SYSTEMS FOR MEASURING ASCORBIC ACID

(71) Applicant: LABORATORY CORPORATION OF AMERICA HOLDINGS, Burlington, NC (US)

(72) Inventors: Russell Phillip Grant, Chapel Hill, NC (US); William Slade, Burlington, NC (US); Erin Fagan, Greensboro, NC (US)

(73) Assignee: Laboratory Corporation of America Holdings, Burlington, NC (US)

( * ) Notice: Subject to any disclaimer, the term of this patent is extended or adjusted under 35 U.S.C. 154(b) by 1077 days.

(21) Appl. No.: 17/273,445

(22) PCT Filed: Oct. 2, 2019

(86) PCT No.: PCT/US2019/054227
§ 371 (c)(1),
(2) Date: Mar. 4, 2021

(87) PCT Pub. No.: WO2020/072595
PCT Pub. Date: Apr. 9, 2020

(65) Prior Publication Data
US 2021/0247401 A1     Aug. 12, 2021

Related U.S. Application Data

(60) Provisional application No. 62/740,732, filed on Oct. 3, 2018.

(51) Int. Cl.
*G01N 33/82*          (2006.01)
*B01J 39/16*          (2017.01)
(Continued)

(52) U.S. Cl.
CPC ............ *C07D 307/60* (2013.01); *B01J 39/16* (2013.01); *C07D 307/62* (2013.01); *G01N 33/82* (2013.01); *G01N 2560/00* (2013.01)

(58) Field of Classification Search
CPC ...... C07D 307/60; C07D 307/62; B01J 39/16; G01N 33/6848; G01N 33/82; G01N 2560/00
See application file for complete search history.

(56) References Cited

U.S. PATENT DOCUMENTS

| | | | |
|---|---|---|---|
| 9,091,695 B2 | 7/2015 | Grant et al. | |
| 2008/0128606 A1 | 6/2008 | Grant et al. | |

(Continued)

FOREIGN PATENT DOCUMENTS

| | | |
|---|---|---|
| CN | 101946005 A | 1/2011 |
| CN | 104040338 A | 9/2014 |

(Continued)

OTHER PUBLICATIONS

Lavoie. Light-induced byproducts of vitamin C in multivitamin solutions. Clinical Chemistry 50:1. 2004. (Year: 2004).*

(Continued)

*Primary Examiner* — Rebecca M Fritchman

(74) *Attorney, Agent, or Firm* — Kilpatrick Townsend & Stockton LLP

(57)          ABSTRACT

Disclosed are methods and systems using liquid chromatography/tandem mass spectrometry (LC-MS/MS and 2D-LC-MS/MS) for the analysis of ascorbic acid in biological samples.

14 Claims, 4 Drawing Sheets

(51) Int. Cl.
  C07D 307/60 (2006.01)
  C07D 307/62 (2006.01)

(56) References Cited

U.S. PATENT DOCUMENTS

| | | | |
|---|---|---|---|
| 2009/0090856 A1 | 4/2009 | Grant et al. | |
| 2010/0084545 A1* | 4/2010 | Jiang | H01J 49/0036 250/282 |
| 2016/0169919 A1* | 6/2016 | Jiang | G01N 30/7233 436/93 |

FOREIGN PATENT DOCUMENTS

| | | |
|---|---|---|
| DE | 4304728 A1 | 8/1994 |
| JP | 2005518401 A | 6/2005 |
| JP | 2016197110 A | 11/2016 |
| JP | 2018506519 | 3/2018 |

OTHER PUBLICATIONS

Bottegel in Analysis of ascorbic acid based black powder substitutes by high-performance liquid chromatography/electrospray ionization quadrupole time-of-flight mass spectrometry and further in view of HE in Extracting Accurate Precursor Information for Tandem Mass Spectra by RawConverter (Year: 2010).*
HE in Extracting Accurate Precursor Information for Tandem Mass Spectra by RawConverter (Year: 2015).*
Canadian Application No. 3,110,921, Office Action mailed on Dec. 16, 2022, 3 pages.
Canadian Application No. 3,110,921, Office Action mailed on Feb. 22, 2022, 3 pages.
Canadian Application No. 3,110,921, Office Action mailed on Oct. 17, 2023, 4 pages.
Chinese Application No. 201980065434.0, Office Action mailed on May 24, 2023, 15 pages (8 pages of Original Document and 7 pages of English Translation).
European Application No. 19791033.4, Office Action mailed on Oct. 2, 2023, 2 pages.
Japanese Application No. 2021518183, Office Action mailed on Mar. 30, 2023, 5 pages (3 pages of Original Document and 2 pages of English Translation).
Japanese Application No. 2021-518183, Notice of Allowance mailed on Sep. 13, 2023, 3 pages.
International Application No. PCT/US2019/054227, International Preliminary Report on Patentability mailed on Apr. 15, 2021, 8 pages.
Deutsch et al., Ascorbate and Dehydroascorbate Measurements in Aqueous Solutions and Plasma Determined by Gas Chromatography-Mass Spectrometry, Analytical Chemistry, vol. 65, No. 4, Feb. 15, 1993, pp. 321-326.
Draisci et al., Quantitation of Anabolic Hormones and Their Metabolites in Bovine Serum and Urine by Liquid Chromatography-Tandem Mass Spectrometry, Journal of Chromatography A, vol. 870, No. 1-2, Feb. 18, 2000, pp. 511-522.
Gentili et al., Simultaneous Determination of Water-Soluble Vitamins in Selected Food Matrices by Liquid Chromatography/Electrospray Ionization Tandem Mass Spectrometry, Rapid Communications in Mass Spectrometry, vol. 22, 2008, pp. 2029-2043.
Polson et al., Optimization of Protein Precipitation Based Upon Effectiveness of Protein Removal and Ionization Effect in Liquid Chromatography-Tandem Mass Spectrometry, Journal of Chromatography B: Analytical Technologies in the Biomedical and Life Sciences, vol. 785, No. 2, Mar. 5, 2003, pp. 263-275.
Salminen et al., Plasma Ascorbic Acid Preparation and Storage for Epidemiological Studies Using TCA Precipitation, Clinical Biochemistry, vol. 41, No. 9, Jun. 2008, pp. 723-727.
Frenich et al., "Determination of Ascorbic Acid and Carotenoids in Food Commodities by Liquid Chromatography with Mass Spectrometry Detection", Journal of Agricultural and Food Chemistry, vol. 53, No. 19, Sep. 1, 2005, pp. 7371-7376.
International Search Report and Written Opinion, Dec. 11, 2019, 11 pages.
Szultka et al., "Determination of Ascorbic Acid and its Degradation Products by High-Performance Liquid Chromatography-Triple Quadrupole Mass Spectrometry : Liquid Phase Separations", Electrophoresis, vol. 35, No. 4, Jan. 13, 2014, pp. 585-592.
Tian et al., "Atmospheric Pressure Chemical Ionization Mass Spectrometry and In-Source Fragmentation of Lutein Esters", Journal of Mass Spectrometry, vol. 38, No. 9, Jan. 1, 2003, pp. 990-995.
CN201980065434.0, "Office Action", dated Nov. 30, 2023, 6 pages.
EP19791033.4, "Intention to Grant", dated Mar. 13, 2024, 9 pages.

\* cited by examiner 3,4-dihydroxyfuran-2(5H)-one m/z 115

(Z)-prop-1-ene-1,2,3-triol diradical m/z 87

(Z)-ethene-1,2-diol radical m/z 59

FIG. 1

METHODS AND SYSTEMS FOR MEASURING ASCORBIC ACID

PRIORITY

The present application claims priority to U.S. Provisional Patent Application No. 62/740,732 filed Oct. 3, 2018, which is hereby incorporated by reference in its entirety herein.

FIELD

The presently disclosed subject matter relates to methods and systems for the analysis of biomarkers. In certain embodiments, the biomarker measurement may be used for clinical diagnosis.

BACKGROUND

Biomarkers, such as hormones, vitamins, metabolites, can be used for the clinical diagnosis of multiple disorders and as biomarkers. For example, the measurement of vitamins, such as Vitamin C, also referred to as ascorbic acid or L-ascorbic acid, can provide key information for patient health. Vitamin C is a water-soluble vitamin that is naturally present in some foods, fortified in others, and available as a dietary supplement alone or in multivitamins. Humans, unlike most animals, cannot synthesize vitamin C de novo and need to obtain it as an essential dietary component. Vitamin C is an essential cofactor for the biosynthesis of a number of critical compounds. It is required for the function of several enzymes involved in the production of collagen, an essential component of connective tissue. These enzymes are required for the molecular cross-linking that gives collagen its elasticity. Vitamin C deficiency renders the polypeptide unstable and unable to self-assemble into rigid triple helices.

Impaired collagen production can result in poor wound healing and a weakening of collagenous structures leading to tooth loss, joint pain, bone and connective tissue pathology, and blood vessel fragility. Vitamin C also serves as a cofactor in the biosynthesis of carnitine, an essential compound for the transport of activated long chain fatty acids into mitochondria. Reduction in carnitine levels due to vitamin C deficiency results in fatigue and lethargy. Vitamin C is an essential cofactor for the conversion of dopamine to norepinephrine, in the metabolism of tyrosine and folate, and in the conversion of cholesterol to bile acids.

Profound and extended vitamin C deficiency leads to scurvy, a condition that is characterized by blood vessel fragility, connective tissue damage, fatigue, and ultimately, death. Early symptoms can include weakness, listlessness, as well as shortness of breath and aching joints, bones, and muscles. Myalgias occur because of the reduced production of carnitine. Oral complications can include gingival bleeding with minor trauma that proceeds to alveolar bone absorption and tooth loss. Rheumatologic problems, such as painful hemarthrosis and subperiosteal hemorrhage, may occur. Cardiac enlargement may occur because of congestive heart failure secondary to high-output anemia. Scurvy manifests when vitamin C intake falls below 10 mg/day for many weeks. Scurvy is rare in developed countries but can still occur in people with limited food variety and in other high-risk groups.

Under physiological conditions, vitamin C serves as a potent antioxidant and has been shown to regenerate other antioxidants, particularly vitamin E. The reduced form of the vitamin, ascorbic acid, is a very effective antioxidant due to its high electron-donating power and ready conversion back to the active reduced form by glutathione. This antioxidant action plays a role in limiting the damage caused by free radicals produced by normal metabolic respiration and might serve to deter the development of certain cancers, cardiovascular disease, and other diseases. Vitamin C concentration has been shown to be inversely associated with all-cause mortality. Low plasma vitamin C concentrations are associated with increased blood pressure, an increased risk of cardiovascular disease, and diabetes.

Thus, there is a need to develop analytical techniques that can be used for the measurement of biomarkers, such as ascorbic acid.

SUMMARY

In some embodiments, a method for determining the presence or amount of ascorbic acid in a sample by tandem mass spectrometry, may comprise: (a) generating a fragment ion from the ascorbic acid of with a mass to charge ratio (m/z) of about 115 by in-source fragmentation; (b) generating one or more product ions of the ascorbic acid fragment ion by tandem mass spectrometry and (c) detecting the presence or amount of one or more of the ascorbic acid fragment ion generated in step (a) or the one or more product ions of step (b) or both, and relating the detected ions to the presence or amount of the ascorbic acid in the sample. For example, during in-source fragmentation, a voltage can be applied to an orifice plate as ions travel from the source into the mass analyzer. In some cases, this voltage can be used to generate fragment ions from the ascorbic acid. In some embodiments, this voltage is called a declustering potential. In some cases, the fragment ions may comprise 3,4-dihydroxyfuran-2 (5H)-one.

In certain embodiments, the product ions of step (b) may comprise ions having a mass/charge ratio (m/z) of about 87 and 59. In some cases, the product ions may comprise at least one of (Z)-prop-1-ene-1,2,3-triol diradical or (Z)-ethene-1,2-diol radical. Optionally, the sample may be heated at the MS/MS interface. In some embodiments, the method may further comprise detection of ascorbic acid over a range of from about 0.05 mg/dL to about 5 mg/dL.

Optionally, the sample may be subjected to a purification step prior to the initial fragmentation step (a). In certain embodiments, the purification step may comprise chromatography, such as high performance liquid chromatography (HPLC). In certain embodiments, the purification step may comprise precipitation of proteins. In some cases, the chromatography may comprise analytical liquid chromatography. In some embodiments, the method may further comprise at least one of liquid-liquid extraction of the sample or dilution of the sample prior to mass spectrometry.

For example, in some embodiments, a method for determining the presence or amount of ascorbic acid in a biological sample, may comprise: providing a biological sample; chromatographically separating the ascorbic acid from other components in the sample; generating a fragment ion of the ascorbic acid; applying the ascorbic acid fragment ion to a mass spectrometer to generate product ions; and analyzing the ascorbic acid fragment ions and/or product ions by mass spectrometry to determine the presence or amount of ascorbic acid in the sample. Optionally, the method may further comprise partially purifying the ascorbic acid by removing proteins by protein precipitation prior to chromatography. In some cases, the ascorbic acid fragment may be made by in-source fragmentation. In certain embodiments, the product ions may comprise ions having a mass/charge ratio (m/z) of about 87 and 59. In some cases, the method may further comprise detection of ascorbic acid over a range of from about 0.05 mg/dL to about 5 mg/dL. In some embodiments, the biological sample may comprise blood, serum, plasma, urine, or saliva.

Also disclosed is a system for determining the presence or amount of ascorbic acid in a test sample. The system may comprise: a station for providing a test sample suspected of containing ascorbic acid; optionally, a station for partially purifying the ascorbic acid from other components in the sample; optionally, a station for chromatographically separating the ascorbic acid from other components in the sample; a station for in-source fragmentation of the ascorbic acid to generate an ascorbic acid fragment ion; and a station for analyzing the ascorbic acid fragment by mass spectrometry to generate product ions from the ascorbic acid fragment ion; and a station to analyze the mass spectrum to determine the presence or amount of ascorbic acid in the test sample. In some embodiments, certain of the stations are combined as a single station. In some cases, the station for in-source fragmentation may be configured to apply a voltage to an orifice plate to generate the ascorbic acid fragment ions. In certain embodiments, at least one of the stations may be controlled by a computer.

BRIEF DESCRIPTION OF THE DRAWINGS

FIG. 1 shows the structures of fragment and product ions in accordance with one embodiment of the present disclosure.

DETAILED DESCRIPTION

Figure 2:
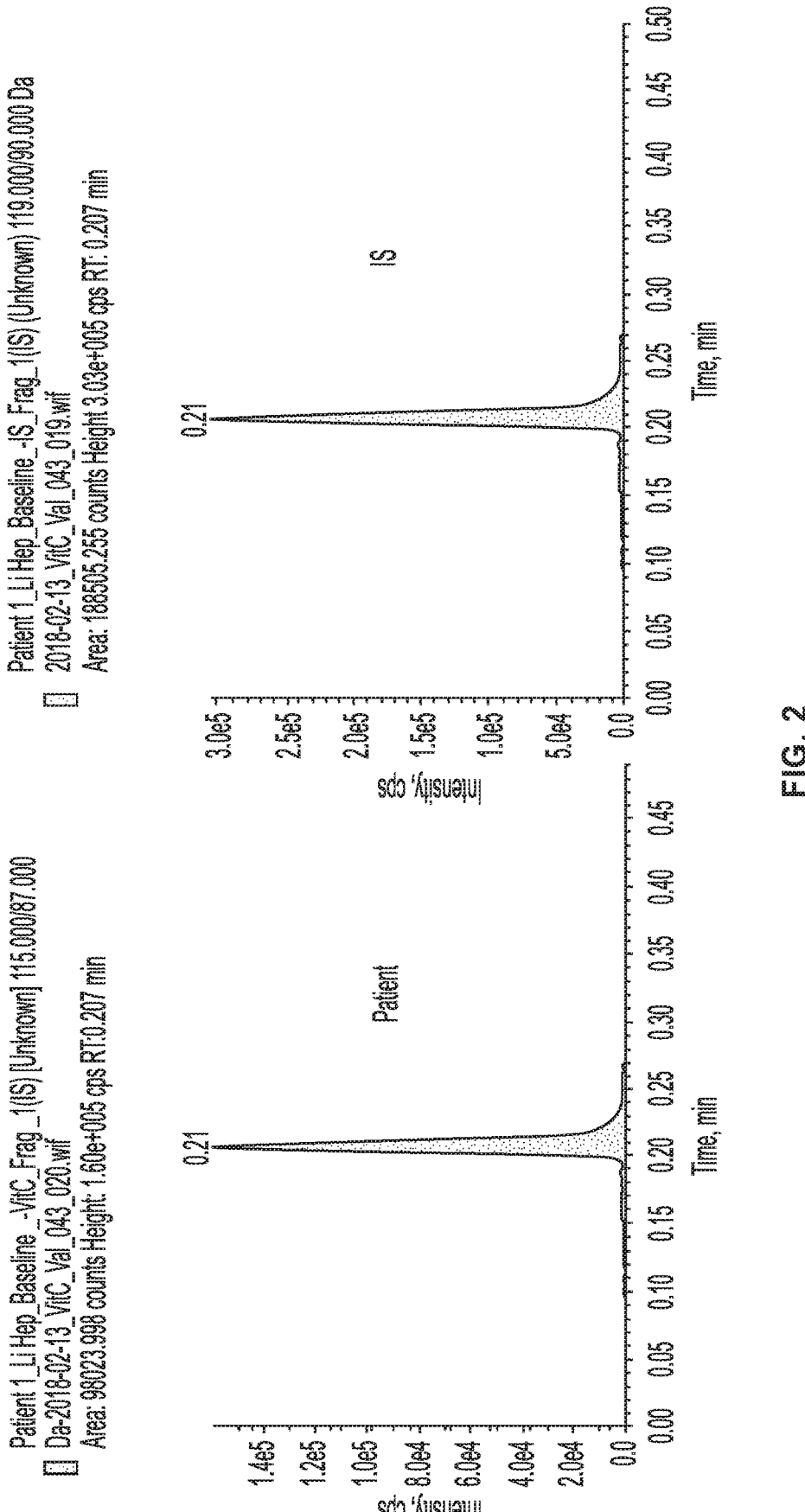
FIG. 2 shows exemplary chromatograms of ascorbic acid analyzed in a patient sample and ascorbic acid internal standard in accordance with one embodiment of the present disclosure.

The presently disclosed subject matter now will be described more fully hereinafter with reference to the accompanying description and drawings, in which some, but not all embodiments of the presently disclosed subject matter are shown. The presently disclosed subject matter can be embodied in many different forms and should not be construed as limited to the embodiments set forth herein. Like numbers refer to like elements throughout.

Many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims. Although specific terms are employed herein, they are used in a generic and descriptive sense only and not for purposes of limitation. The disclosure utilizes the abbreviations shown below.

Abbreviations

| | | |
|---|---|---|
| APCI | = | atmospheric pressure chemical ionization |
| HTLC | = | high turbulence (throughput) liquid chromatography |
| HPLC | = | high performance liquid chromatography |
| LLE | = | liquid-liquid extraction |
| LOQ | = | limits of quantification |
| LLOQ | = | lower limit of quantification |
| SST | = | system suitability test |
| ULOQ | = | upper limit of quantification |
| 2D-LC-MS/MS | = | two-dimensional liquid chromatography hyphenated to tandem mass spectrometry |
| (LC)-LC-MS/MS | = | two-dimensional liquid chromatography tandem hyphenated to mass spectrometry |
| (LC)-MS/MS | = | liquid chromatography hyphenated to tandem mass spectrometry |

Definitions and Descriptions

While the following terms are believed to be well understood by one of ordinary skill in the art, the following definitions are set forth to facilitate explanation of the presently disclosed subject matter. Other definitions are found throughout the specification. Unless otherwise defined, all technical and scientific terms used herein have the same meaning as commonly understood by one of ordinary skill in the art to which this presently described subject matter belongs.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10. Additionally, any reference referred to as being "incorporated herein" is to be understood as being incorporated in its entirety.

The terms "a", "an", and "the" refer to "one or more" when used in this application, including the claims. Thus, for example, reference to "a cell" includes a plurality of such cells, unless the context clearly is to the contrary (e.g., a plurality of cells), and so forth.

As used herein Vitamin C, is interchangeable with the terms ascorbic acid or L-ascorbic acid.

As used herein, the terms "purify" or "separate" or derivations thereof do not necessarily refer to the removal of all materials other than the analyte(s) of interest from a sample matrix. Instead, in some embodiments, the terms "purify" or "separate" refer to a procedure that enriches the amount of one or more analytes of interest relative to one or more other components present in the sample matrix. In some embodiments, a "purification" or "separation" procedure can be used to remove one or more components of a sample that could interfere with the detection of the analyte, for example, one or more components that could interfere with detection of an analyte by mass spectrometry.

As used herein, "chromatography" refers to a process in which a chemical mixture carried by a liquid or gas is separated into components as a result of differential distribution of the chemical entities as they flow around or over a stationary liquid or solid phase.

As used herein, "liquid chromatography" (LC) means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). "Liquid chromatography" includes reverse phase liquid chromatography (RPLC), high performance liquid chromatography (HPLC) and high turbulence liquid chromatography (HTLC).

As used herein, the term "HPLC" or "high performance liquid chromatography" refers to liquid chromatography in which the degree of separation is increased by forcing the mobile phase under pressure through a stationary phase, typically a densely packed column. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties such as the biomarker analytes quantified in the experiments herein. One suitable bonded surface is a hydrophobic bonded surface such as an alkyl bonded surface. Alkyl bonded surfaces may include C-4, C-8, or C-18 bonded alkyl groups, preferably C-18 bonded groups. The chromatographic column includes an inlet port for receiving a sample and an outlet port for discharging an effluent that includes the fractionated sample. In the method, the sample (or pre-purified sample) may be applied to the column at the inlet port, eluted with a solvent or solvent mixture, and discharged at the outlet port. Different solvent modes may be selected for eluting different analytes of interest. For example, liquid chromatography may be performed using a gradient mode, an isocratic mode, or a polytyptic (i.e. mixed) mode.

As used herein, the term "analytical column" refers to a chromatography column having sufficient chromatographic plates to effect a separation of the components of a test sample matrix. Preferably, the components eluted from the analytical column are separated in such a way to allow the presence or amount of an analyte(s) of interest to be determined. In some embodiments, the analytical column comprises particles having an average diameter of about 5 μm. In some embodiments, the analytical column is a functionalized silica or polymer-silica hybrid, or a polymeric particle or monolithic silica stationary phase, such as a phenyl-hexyl functionalized analytical column.

Analytical columns can be distinguished from "extraction columns," which typically are used to separate or extract retained materials from non-retained materials to obtained a "purified" sample for further purification or analysis.

The term "heart-cutting" refers to the selection of a region of interest in a chromatogram and subjecting the analytes eluting within that region of interest to a second separation, e.g., a separation in a second dimension.

The term "biomarker" or "marker" as used herein refers to one or more nucleic acids, polypeptides and/or other biomolecules (e.g., vitamin C, hormones, or other small molecules) that can be used to diagnose, or to aid in the diagnosis or prognosis of a disease or syndrome of interest, either alone or in combination with other biomarkers; monitor the progression of a disease or syndrome of interest; and/or monitor the effectiveness of a treatment for a syndrome or a disease of interest.

The term "electron ionization" as used herein refers to methods in which an analyte of interest in a gaseous or vapor phase interacts with a flow of electrons. Impact of the electrons with the analyte produces analyte ions, which may then be subjected to a mass spectrometry technique.

The term "chemical ionization" as used herein refers to methods in which a reagent gas (e.g. ammonia) is subjected to electron impact, and analyte ions are formed by the interaction of reagent gas ions and analyte molecules.

The term "field desorption" as used herein refers to methods in which a non-volatile test sample is placed on an ionization surface, and an intense electric field is used to generate analyte ions.

The term "matrix-assisted laser desorption ionization," or "MALDI" as used herein refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

The term "surface enhanced laser desorption ionization," or "SELDI" as used herein refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

The term "electrospray ionization," or "ESI," as used herein refers to methods in which a solution is passed along a short length of capillary tube, to the end of which is applied a high positive or negative electric potential. Upon reaching the end of the tube, the solution may be vaporized (nebulized) into a jet or spray of very small droplets of solution in solvent vapor. This mist of droplet can flow through an evaporation chamber which is heated slightly to prevent condensation and to evaporate solvent. As the droplets get smaller the electrical surface charge density increases until such time that the natural repulsion between like charges causes ions as well as neutral molecules to be released.

The term "Atmospheric Pressure Chemical Ionization," or "APCI," as used herein refers to mass spectroscopy methods that are similar to ESI, however, APCI produces ions by ion-molecule reactions that occur within a plasma at atmospheric pressure. The plasma is maintained by an electric discharge between the spray capillary and a counter electrode. Then, ions are typically extracted into a mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "Atmospheric Pressure Photoionization" ("APPI") as used herein refers to the form of mass spectroscopy where the mechanism for the photoionization of molecule Mis photon absorption and electron ejection to form the molecular M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+ (see e.g., Robb et al., 2000, Anal. Chem. 72 (15): 3653-3659).

The term "inductively coupled plasma" as used herein refers to methods in which a sample is interacted with a partially ionized gas at a sufficiently high temperature to atomize and ionize most elements.

The term "ionization" and "ionizing" as used herein refers to the process of generating an analyte ion having a net electrical charge equal to one or more electron units. Negative ions are those ions having a net negative charge of one or more electron units, while positive ions are those ions having a net positive charge of one or more electron units.

The term "in source fragmentation" as used herein refers to applying a voltage to an orifice plate as ions travel from the source into the mass analyzer. In some embodiments, this voltage is called a declustering potential.

The term "desorption" as used herein refers to the removal of an analyte from a surface and/or the entry of an analyte into a gaseous phase.

As used herein, the term "biological sample" refers to a sample obtained from a biological source, including, but not limited to, an animal, a cell culture, an organ culture, and the like. Suitable samples include blood, plasma, serum, urine, saliva, tear, cerebrospinal fluid, organ, hair, muscle, or other tissue sample.

As used herein, a subject may comprise an animal. Thus, in some embodiments, the biological sample is obtained from a mammalian animal, including, but not limited to a dog, a cat, a horse, a rat, a monkey, and the like. In some embodiments, the biological sample is obtained from a human subject. In some embodiments, the subject is a patient, that is, a living person presenting themselves in a clinical setting for diagnosis, prognosis, or treatment of a disease or condition. In some embodiments, the test sample is not a biological sample, but comprises a non-biological sample, e.g., obtained during the manufacture or laboratory analysis of a vitamin, which can be analyzed to determine the composition and/or yield of the manufacturing and/or analysis process.

Methods of Analysis of Biomarkers by LC-MS/MS

Thus, embodiments of the present disclosure relate to methods and systems for the quantitative analysis of biomarkers for clinical diagnosis. The present disclosure may be embodied in a variety of ways.

In one embodiment, the present disclosure comprises a method for determining the presence or amount of at least one biomarker of interest in a biological sample, the method comprising: providing a biological sample believed to contain at least one biomarker of interest; optionally, chromatographically separating the at least one biomarker of interest from other components in the sample; generating a fragment ion of the at least one biomarker of interest; applying the fragment ion to a mass spectrometer to generate product ions; and analyzing the fragment and/or product ions to determine the presence or amount of the at least one biomarker of interest in the sample. In some cases, the fragment ion may be made by in-source fragmentation. During in-source fragmentation, a voltage can be applied to an orifice plate as ions travel from the source into the mass analyzer. In some embodiments, this voltage can be used to generate fragment ions from the biomarker of interest. In some cases, this voltage is called a declustering potential. In an embodiment, the at least one biomarker comprises Vitamin C, also known as ascorbic acid or L-ascorbic acid.

In certain embodiments, the chromatography may comprise high performance liquid chromatography (HPLC). In an embodiment, the chromatography may comprises extraction and/or analytical liquid chromatography.

In an embodiment, the method may comprise purifying the biomarker of interest prior to chromatography. For example, the sample may be partially purified by at least one of liquid-liquid extraction or protein precipitation. Also, the method may comprise the step of diluting the sample into a solvent or solvents used for LS and/or MS.

In some embodiments, the method may comprise the use of two liquid chromatography steps. For example, in certain embodiments, the method for determining the presence or amount of one or more biomarkers in a test sample may comprise the steps of: (a) providing a sample suspected of containing one or more biomarkers of interest; (b) partially purifying the one or more biomarkers of interest from other components in the sample by at least one of liquid-liquid extraction, protein precipitation, or by diluting the sample; (c) transferring the one or more biomarkers of interest to an analytical column and chromatographically separating the one or more biomarkers of interest from other components in the sample; and (d) analyzing the chromatographically separated biomarkers of interest by mass spectrometry to determine the presence or amount of the one or more biomarkers in the test sample. In an embodiment, the at least one biomarker comprises Vitamin C, also known as ascorbic acid or L-ascorbic acid.

Thus, in certain embodiments, the present disclosure comprises methods for measuring ascorbic acid in a sample. For example, in one embodiment, the present disclosure comprises a method for determining the presence or amount of ascorbic acid in a sample by tandem mass spectrometry, comprising: (a) generating a fragment ion from the ascorbic acid; (b) generating one or more product ions of the ascorbic acid fragment ion by tandem mass spectrometry; and (c) detecting the presence or amount of one or more of ascorbic acid fragment ion generated in step (a) or the product ions generated in step (b) or both, and relating the detected ions to the presence or amount of the ascorbic acid in the sample.

During in-source fragmentation, a voltage can be applied to an orifice plate as ions travel from the source into the mass analyzer. In some cases where the biomarker of interest is ascorbic acid, the voltage may generate fragment ions from ascorbic acid. In some embodiments, the treatment of ascorbic acid by in-source fragmentation reduces the molecular weight of the ascorbic acid by about 60 mass units. Thus, in an embodiment, the ascorbic acid fragment ion has a mass/charge ratio (m/z) of about 115. In an embodiment the product ions comprise ions having a mass/charge ratio (m/z) of about 87 and about 59.

Figure 1:
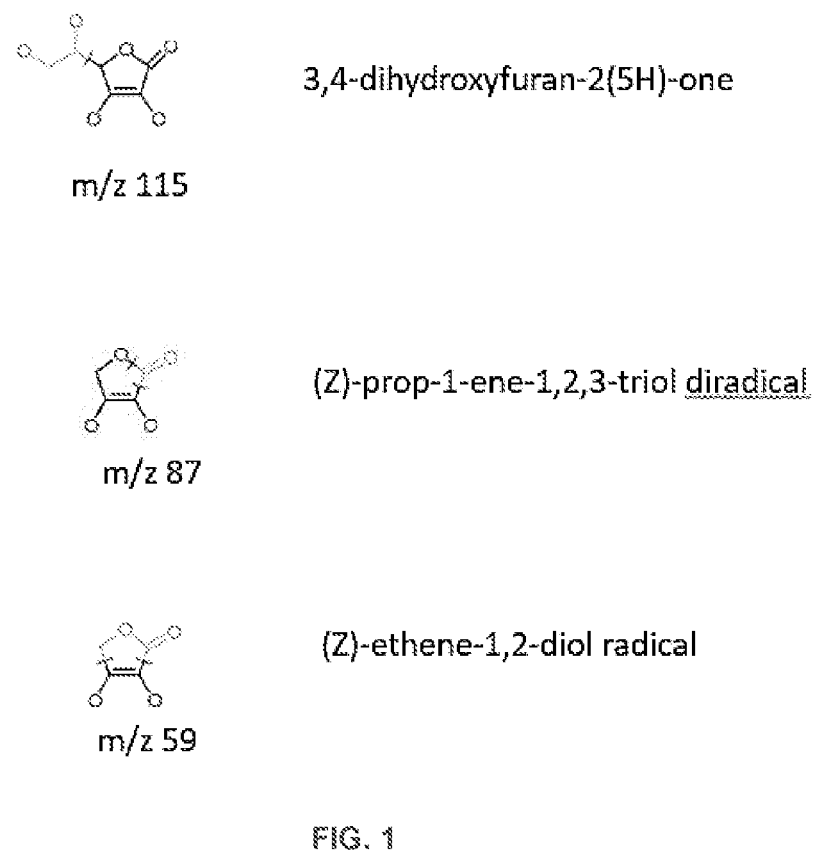

In certain embodiments, the fragment ion can comprise 3,4-dihyroxyfuran-2 (5H)-one. The product ions can comprise at least one of (Z)-prop-1-ene-1,2,3-triol diradical or (Z)-ethene-1,2-diol radical. FIG. 1 shows the structures and related m/z ratios for these fragment and product ions.

The method may comprise detection of ascorbic acid over a range of from a LLOQ of about 0.05 mg/dL to an ULOQ of about 5 mg/dL as a single assay (i.e., as a linear assay without multiple dilution of the samples). Samples above the ULOQ may be diluted up to 10× pre-extraction with a blank solution of 1% Bovine Serum Albumin (w/v), 0.1% Sodium Metabisulfite (w/v) in Tris-Acetate. FIG. 2 shows the chromatograms of ascorbic acid in a patient sample and comparison internal standard of ascorbic acid.

In an embodiment, the sample may be subjected to a purification step prior to initial fragmentation step by in-source fragmentation. For example, in certain embodiments, the purification step may comprise chromatography and/or precipitation of proteins. As discussed herein, in certain embodiments, the chromatography comprises high performance liquid chromatography (HPLC). The LC step may comprise one LC separation, or multiple LC separations. In one embodiment, the chromatographic separation comprises extraction and analytical liquid chromatography. Additionally or alternatively, high turbulence liquid chromatography (HTLC) (also known as high throughput liquid chromatography) may be used.

The purification may comprise steps in addition to HPLC or other types of chromatographic separation techniques. In alternate embodiments, the method may comprise at least one of liquid-liquid extraction or dilution. In one embodiment, the sample is diluted into a solvent or solvent mixture that may be used for LC and/or MS (e.g., LC-MS/MS or 2D-LC-MS/MS).

In some embodiments, an isotope of the biomarker of interest may be added as an internal standard. For example, stable labeled isotope for ascorbic acid may be added as an internal standard to sample aliquots. In some cases, after addition of internal standard and mixing, 10% Trichloroacetic acid (TCA) may be added as a precipitating solution to sample aliquots. The samples may be mixed, centrifuged, and supernatant transferred to a clean well plate of a LC-MS/MS system. In some cases, the plate may be a 2 mL 96-well plate containing acetonitrile. The sample may be then injected onto a LC-MS/MS system. One example of a LC-MS/MS system is an MDS-Sciex API5500 triple quadrupole mass spectrometer, which may be operated in negative ion electrospray ionization mode for detection. In some embodiments, quantification of analyte and internal standards may be performed in selected reaction monitoring mode (SRM). The back-calculated amount of the ascorbic acid in each sample can be determined from a calibration curve generated by spiking known amounts of purified ascorbic acid into 1% (w/v) BSA in Tris-Acetate, pH 6.0, 0.1% (w/v) Sodium Metabisulfite from 0.05-5.0 mg/dL.

Figure 3:
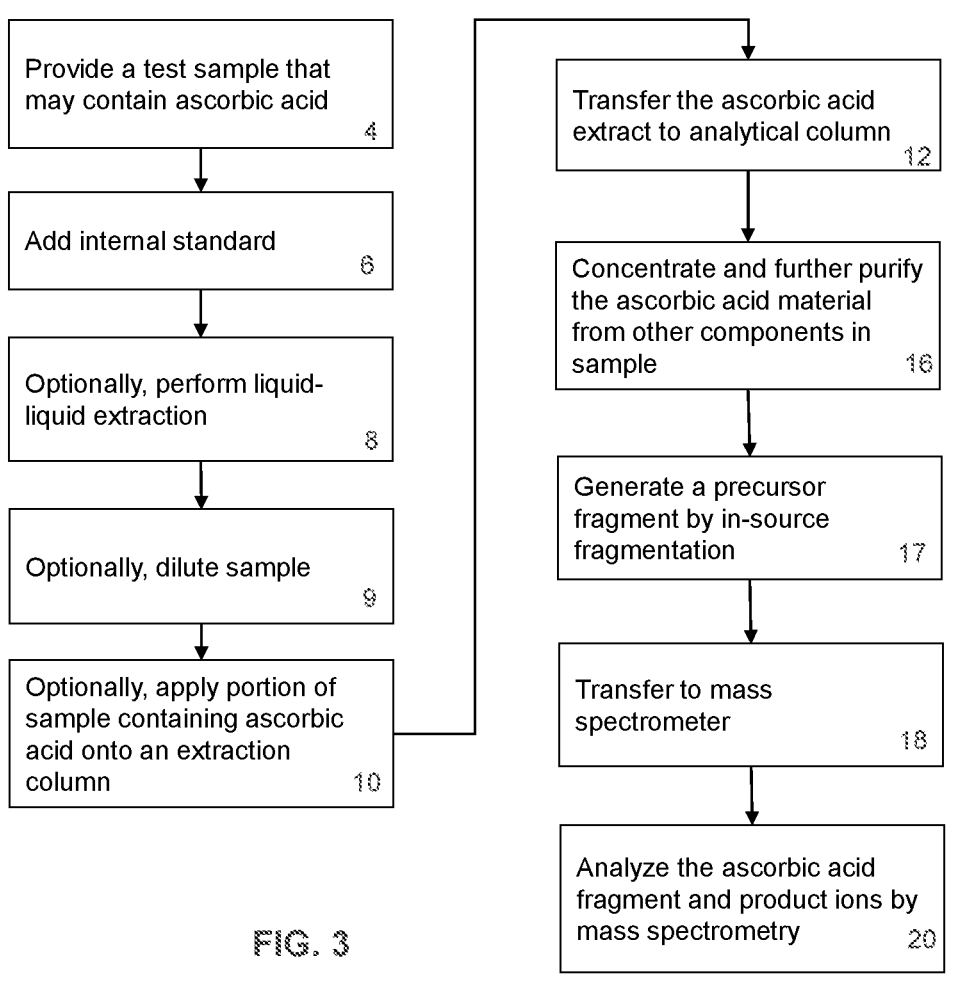
FIG. 3 shows a flow chart of a method for quantitative analysis of ascorbic acid in accordance with one embodiment of the present disclosure.

An example of a method of the present disclosure is shown in FIG. 3. Thus, in an embodiment, the method may include a step of providing a biological sample, for example, a serum sample believed to contain ascorbic acid (4). The samples and calibrators may degrade with UV exposure and require light protection and may require foil covering, amber bottles, or other packaging to be light-protected. In some embodiments, an appropriate internal standard is added to the sample (6). For example, in some embodiments of the presently disclosed method for analyzing ascorbic acid in serum samples, $C_{13}$-L-ascorbic acid labeled isotopes may be used.

In some embodiments, the ascorbic acid may be partially purified by liquid-liquid extraction of the sample (8). Or, the sample may be diluted (9) in a solvent that can be used for LC or MS in subsequent purification steps. Or the sample may be partially purified by protein precipitation.

Where the sample is extracted, the internal standard addition may include a stabilizing agent such as trichloroacetic acid (TCA). Where extraction is not performed, the internal standard may be added in acetonitrile or a similar solvent used for LC. In some embodiments, ascorbic acid can be extracted from a serum sample with an organic solvent. In some embodiments, extracted ascorbic acid can be diluted with an organic solvent. For example, in an embodiment, an alkane mixed with a more polar solvent is used. In an embodiment, a 1:4 10% TCA:acetonitrile solution may be used.

Still referring to FIG. 3, the method may further include liquid chromatography as a means to separate the biomarker from other components in the sample. In an embodiment, two liquid chromatography steps are used. For example, the method may comprise a first extraction column liquid chromatography (10), transfer of ascorbic acid to a second analytical column (12), and an analytical column liquid chromatography (16). In other embodiments, only one liquid chromatography step is used.

The first extraction liquid chromatography column may, in certain embodiments, comprise a step whereby the biomarkers (i.e., analytes of interest) are separated from a majority of contaminants. Thus, in certain embodiments, the first column provides the majority of selectivity for the procedure. The second analytical liquid chromatography column may, in certain embodiments, comprise a step whereby the biomarkers are concentrated, to thereby increase sensitivity for analysis by mass spectrometry (MS).

Depending upon the biomarker of interest, a variety of analytical columns known in the art may be used as needed to provide good purification. In certain embodiments, the analytical column may comprise particles having an average diameter of about 3 μm. In some embodiments, the analytical column is a functionalized silica or polymer-silica hybrid, or a polymeric particle or monolithic silica stationary phase, such as a phenyl-hexyl functionalized analytical column.

If two liquid chromatography steps are employed, the eluted analytes may be transferred to the analytical column in a manner such that the sample is concentrated upon application to the analytical column. In some embodiments, the eluted analytes are transferred to the analytical column via a heart-cutting technique. In some embodiments, a chromato-focusing procedure is used to transfer and focus the analytes on the analytical column. Also in some embodiments, a column-switching procedure is used to transfer the analytes to the analytical column. The analytes may then be separated on the analytical column (16) and the fraction containing the analyte of interest is eluted. In an embodiment, the second column in run in a manner to maximize throughput, and to provide the sample in a reduced volume.

The separated analytes are then fragmented by in-source fragmentation (17). The fragmented ions are introduced into a mass spectrometer (MS) system (18). In some embodiments, a tandem MS/MS system is used. As is known by those of skill in the art, in tandem MS spectrometry, the precursor ion is selected following ionization, and that precursor ion is subjected to additional fragmentation to generate product ions, whereby one or more product ions are selected for detection.

The analyte of interest may then be quantified based upon the amount of the characteristic transitions measured by tandem MS (20). In some embodiments, the tandem mass spectrometer comprises a triple quadrupole mass spectrometer. In some embodiments, the tandem mass spectrometer is operated in a positive ion Atmospheric Pressure Chemical Ionization (APCI) mode. In some embodiments, the quantification of the analytes and internal standards is performed in the selected reaction monitoring mode (SRM). Or, other methods of ionization such as the use of inductively coupled plasma, or MALDI, or SELDI, ESI, or APPI may be used for ionization.

In some embodiments, the back-calculated amount of each analyte in each sample may be determined by comparison of unknown sample response or response ratio when employing internal standardization to calibration curves generated by spiking a known amount of purified analyte material into a standard test sample, e.g., charcoal stripped human serum. In one embodiment, calibrators are prepared at known concentrations and analyzed as per the biomarker methodology to generate a response or response ratio when employing internal standardization versus concentration calibration curve.

Thus, the methods provide the ability to quantify ascorbic acid at physiologically relevant levels. As discussed herein, the difference between a serum level of 0.05 mg/dL and 2500 mg/dL may be clinically relevant. In one embodiment, the method is able to report ascorbic acid at these levels, with dilution necessary for measurements at levels above 5 mg/dL.

Systems for Analysis of A Biomarker of Interest

In other embodiments, the present disclosure comprises a system for determining the presence or amount of one or more biomarkers in a sample. For example, in some embodiments, the system may comprise: a station for providing a sample believed to contain at least one biomarker of interest; optionally, a station for chromatographically separating the at least one biomarker of interest from other components in the sample; a station for in-source fragmentation of the at least one biomarker; and a station for mass spectrometry to generate production ions from the fragment ion; and a station to analyze the mass spectrometry results determine the presence or amount of the one or more biomarkers in the sample. In some embodiments, the station for in-source fragmentation may be configured to apply a voltage to an orifice plate to generate the fragment ions. In an embodiment, the biomarker of interest is ascorbic acid.

In an embodiment, the system may also comprise a station for partially purifying the at least one biomarker of interest from other components in the sample. In an embodiment, the mass spectrometry is operated in an atmospheric pressure chemical ionization (APCI) mode. Also in certain embodiments, at least one of the stations is automated and/or controlled by a computer. For example, as described herein, in certain embodiments, at least some of the steps are automated such that little to no manual intervention is required.

In one embodiment, the station for chromatographic separation comprises at least one apparatus to perform liquid chromatography (LC). In one embodiment, the station for liquid chromatography comprises a column for extraction chromatography. Additionally or alternatively, the station for liquid chromatography may comprise a column for analytical chromatography. In certain embodiments, the column for extraction chromatography and analytical chromatography comprise a single station or single column. For example, in one embodiment, liquid chromatography is used to purify the biomarker of interest from other components in the sample that co-purify with the biomarker of interest after extraction or dilution of the sample.

The system may also include a station for analyzing the fragment ion and/or product ions of the one or more biomarkers of interest by mass spectrometry to determine the presence or amount of the one or more biomarkers in the test sample. In certain embodiments, tandem mass spectrometry is used (MS/MS). For example, in certain embodiments, the station for tandem mass spectrometry comprises an Applied Biosystems API4000 or API5000 or thermo quantum or Agilent 7000 triple quadrupole mass spectrometer.

The system may also comprise a station for extracting the biomarker of interest (e.g., ascorbic acid) from the test sample and/or diluting the sample. In an embodiment, the station for extraction comprises a station for liquid-liquid extraction. The station for liquid-liquid extraction may comprise equipment and reagents for addition of solvents to the sample and removal of waste fractions. In some cases a isotopically-labeled internal standard is used to standardize losses of the biomarker that may occur during the procedures. Thus, the station for liquid-liquid extraction may comprise a hood or other safety features required for working with solvents.

In certain embodiments, the methods and systems of the present disclosure may comprise multiple liquid chromatography steps. Thus, in certain embodiments, a two-dimensional liquid chromatography (LC) procedure is used. For example, in one embodiment, the method and systems of the present disclosure may comprise transferring the biomarker of interest from the LC extraction column to an analytical column. In one embodiment, the transferring of the at least one biomarker of interest from the extraction column to an analytical column is done by a heart-cutting technique. In another embodiment, the biomarker of interest is transferred from the extraction column to an analytical column by a chromato-focusing technique. Alternatively, the biomarker of interest is transferred from the extraction column to an analytical column by a column switching technique. These transfer steps may be done manually, or may be part of an on-line system. Optionally, an extraction column may not be used in the methods and systems described herein.

Various columns comprising stationary phases and mobile phases that may be used for extraction or analytical liquid chromatography are described herein. The column used for optional extraction liquid chromatography may be varied depending on the biomarker of interest. The column used for analytical liquid chromatography may be varied depending on the biomarker of interest and/or the column that was used for the extraction liquid chromatography step. For example, in certain embodiments, the analytical column comprises particles having an average diameter of about 3 μm. In some embodiments, the analytical column is a functionalized silica or polymer-silica hybrid, or a polymeric particle or monolithic silica stationary phase, such as a phenyl-hexyl functionalized analytical column.

In certain embodiments, the mass spectrometer may comprise a tandem mass spectrometer (MS/MS). For example, in one embodiment of the methods and systems of the present disclosure, the tandem MS/MS spectrometry comprises a triple quadrupole tandem mass spectrometer.

The tandem MS/MS may be operated in a variety of modes. In one embodiment, the tandem MS/MS spectrometer is operated in an atmospheric pressure chemical ionization (APCI) mode. In some embodiments, the quantification of the analytes and internal standards is performed in the selected reaction monitoring mode (SRM).

In an embodiment, an extraction may be used to concentrate and partially purify the analyte. For example, when the biomarker is ascorbic acid, ascorbic acid can be extracted from a serum sample with an organic solvent such as trichloroacetic acid (TCA). In some embodiments, extracted ascorbic acid can be diluted with an organic solvent. In some embodiments, an alkane mixed with a more polar solvent can be used. In an embodiment, a 1:4 10% TCA:acetonitrile solution may be used.

Where the sample is extracted, the internal standard addition may include a stabilizing agent such as trichloroacetic acid (TCA). Where extraction is not performed, the internal standard may be added in acetonitrile or a similar solvent used for LC.

Figure 4:
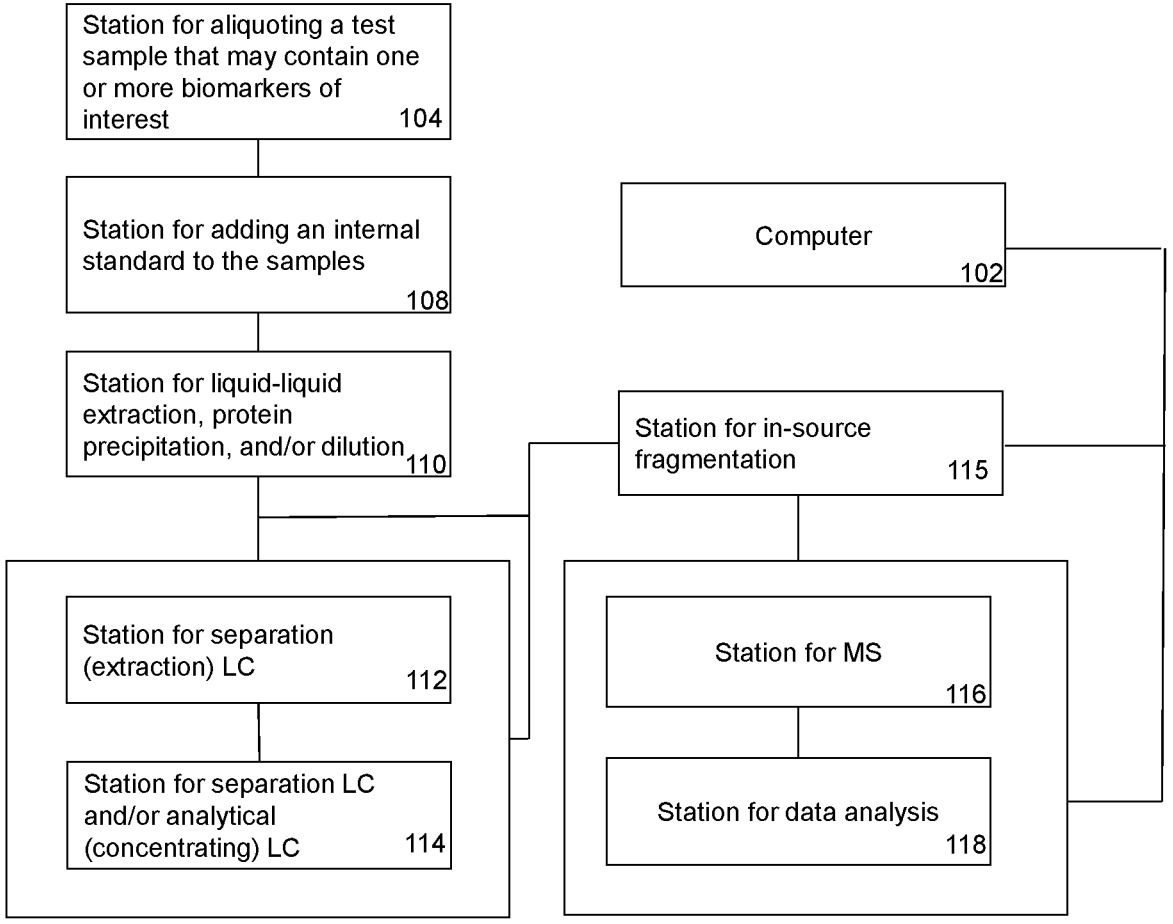
FIG. 4 shows a system for quantitative analysis of a biomarker of interest in accordance with one embodiment of the present disclosure.

FIG. 4 provides a drawing of an embodiment of a system of the disclosure. As shown in FIG. 4, the system may comprise a station for aliquoting a sample (104) that may comprise a biomarker of interest into sampling containers. In one embodiment, the sample is aliquoted into a container or containers to facilitate liquid-liquid extraction or sample dilution. The station for aliquoting may comprise receptacles to discard the portion of the biological sample that is not used in the analysis.

The system may further comprise a station for adding an internal standard to the sample (108). In an embodiment, the internal standard comprises the biomarker of interest labeled with a non-natural isotope. Thus, the station for adding an internal standard may comprise safety features to facilitate adding an isotopically labeled internal standard solutions to the sample. The system may also, in some embodiments, comprise a station for liquid-liquid extraction, protein precipitation and/or dilution of the sample (110).

The system may also comprise a station for liquid chromatography (LC) of the sample. As described herein, in an embodiment, the station for liquid chromatography may comprise an extraction liquid chromatography column (112). The station for liquid chromatography may comprise a column comprising the stationary phase, as well as containers or receptacles comprising solvents that are used as the mobile phase. In an embodiment, the mobile phase comprises a gradient of acetonitrile, ammonium formate, and water, or other miscible solvents with aqueous volatile buffer solutions. Thus, in one embodiment, the station may comprise the appropriate lines and valves to adjust the amounts of individual solvents being applied to the column or columns. Also, the station may comprise a means to remove and discard those fractions from the LC that do not comprise the biomarker of interest. In an embodiment, the fractions that do not contain the biomarker of interest are continuously removed from the column and sent to a waste receptacle for decontamination and to be discarded.

A variety of extraction LC systems may be used. For example, in the embodiment where the system is being used to measure ascorbic acid, a extraction column with an analytical column, with mobile phases comprising a gradient of acetonitrile and water are used.

The system may also comprise an analytical LC column (114). The analytical column may facilitate further purification and concentration of the biomarker of interest as may be required for further characterization and quantification.

Also, the system may comprise a station for characterization and quantification of the biomarker of interest. In one embodiment, the system may comprise a station for in-source fragmentation of the biomarker of interest (115). In one embodiment, the system may comprise a station for mass spectrometry (MS) of the biomarker (116). In an embodiment, the station for mass spectrometry comprises a station for tandem mass spectrometry (MS/MS). Also, the station for characterization and quantification may comprise a computer and software for analysis of the MS/MS results (118). In an embodiment, the analysis comprises both identification and quantification of the biomarker of interest.

In some embodiments, one or more of the purification or separation steps can be performed "on-line." As used herein, the term "on-line" refers to purification or separation steps that are performed in such a way that the test sample is disposed, e.g., injected, into a system in which the various components of the system are operationally connected and, in some embodiments, in fluid communication with one another. The on-line system may comprise an autosampler for removing aliquots of the sample from one container and transferring such aliquots into another container. For example, an autosampler may be used to transfer the sample after extraction onto an LC extraction column. Additionally or alternatively, the on-line system may comprise one or more injection ports for injecting the fractions isolated from the LC extraction columns onto the LC analytical column. Additionally or alternatively, the on-line system may comprise one or more injection ports for injecting the LC purified sample into the MS system. Thus, the on-line system may comprise one or more columns, including but not limited to, an extraction column, including an HTLC extraction column, and in some embodiments, an analytical column. Additionally or alternatively, the system may comprise a detection system, e.g., a mass spectrometer system. The on-line system may also comprise one or more pumps; one or more valves; and necessary plumbing. In such "on-line" systems, the test sample and/or analytes of interest can be passed from one component of the system to another without exiting the system, e.g., without having to be collected and then disposed into another component of the system.

In some embodiments, the on-line purification or separation method can be automated. In such embodiments, the steps can be performed without the need for operator intervention once the process is set-up and initiated. For example, in one embodiment, the system, or portions of the system may be controlled by a computer or computers (102). Thus, in certain embodiments, the present disclosure may comprise software for controlling the various components of the system, including pumps, valves, autosamplers, and the like. Such software can be used to optimize the extraction process through the precise timing of sample and solute additions and flow rate.

Although some or all of the steps in the method and the stations comprising the system may be on-line, in certain embodiments, some or all of the steps may be performed "off-line." In contrast to the term "on-line", the term "off-line" refers to a purification, separation, or extraction procedure that is performed separately from previous and/or subsequent purification or separation steps and/or analysis steps. In such off-line procedures, the analytes of interests typically are separated, for example, on an extraction column or by liquid/liquid extraction, from the other components in the sample matrix and then collected for subsequent introduction into another chromatographic or detector system. Off-line procedures typically require manual intervention on the part of the operator.

Liquid chromatography may, in certain embodiments, comprise high turbulence liquid chromatography or high throughput liquid chromatography (HTLC). See, e.g., Zimmer et al., J. Chromatogr. A 854:23-35 (1999); see also, U.S. Pat. Nos. 5,968,367; 5,919,368; 5,795,469; and 5,772,874. Traditional HPLC analysis relies on column packings in which laminar flow of the sample through the column is the basis for separation of the analyte of interest from the sample. In such columns, separation is a diffusional process. Turbulent flow, such as that provided by HTLC columns and methods, may enhance the rate of mass transfer, improving the separation characteristics provided. In some embodiments, high turbulence liquid chromatography (HTLC), alone or in combination with one or more purification methods, may be used to purify the biomarker of interest prior to mass spectrometry. In such embodiments, samples may be extracted using an HTLC extraction cartridge which captures the analyte, then eluted and chromatographed on a second HTLC column or onto an analytical HPLC column prior to ionization. Because the steps involved in these chromatography procedures can be linked in an automated fashion, the requirement for operator involvement during the purification of the analyte can be minimized. Also, in some embodiments, the use of a high turbulence liquid chromatography sample preparation method can eliminate the need for other sample preparation methods including liquid-liquid extraction. Thus, in some embodiments, the test sample, e.g., a biological fluid, can be disposed, e.g., injected, directly onto a high turbulence liquid chromatography system.

For example, in a typical high turbulence or turbulent liquid chromatography system, the sample may be injected directly onto a narrow (e.g., 0.5 mm to 2 mm internal diameter by 20 to 50 mm long) column packed with large (e.g., >25 micron) particles. When a flow rate (e.g., 3-500 mL per minute) is applied to the column, the relatively narrow width of the column causes an increase in the velocity of the mobile phase. The large particles present in the column can prevent the increased velocity from causing back pressure and promote the formation of vacillating eddies between the particles, thereby creating turbulence within the column.

In high turbulence liquid chromatography, the analyte molecules may bind quickly to the particles and typically do not spread out, or diffuse, along the length of the column. This lessened longitudinal diffusion typically provides better, and more rapid, separation of the analytes of interest from the sample matrix. Further, the turbulence within the column reduces the friction on molecules that typically occurs as they travel past the particles. For example, in traditional HPLC, the molecules traveling closest to the particle move along the column more slowly than those flowing through the center of the path between the particles. This difference in flow rate causes the analyte molecules to spread out along the length of the column. When turbulence is introduced into a column, the friction on the molecules from the particle is negligible, reducing longitudinal diffusion.

The methods and systems of the present disclosure may use mass spectrometry to detect and quantify the biomarker of interest. The terms "mass spectrometry" or "MS" as used herein generally refer to methods of filtering, detecting, and measuring ions based on their mass-to-charge ratio, or "m/z." In MS techniques, one or more molecules of interest are ionized, and the ions are subsequently introduced into a mass spectrometer where, due to a combination of electric fields, the ions follow a path in space that is dependent upon mass ("m") and charge ("z").

In certain embodiments, the mass spectrometer uses a "quadrupole" system. In a "quadrupole" or "quadrupole ion trap" mass spectrometer, ions in an oscillating radio frequency (RF) field experience a force proportional to the direct current (DC) potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

In certain embodiments, tandem mass spectrometry is used. See, e.g., U.S. Pat. No. 6,107,623, entitled "Methods and Apparatus for Tandem Mass Spectrometry," which is hereby incorporated by reference in its entirety. Further, the selectivity of the MS technique can be enhanced by using "tandem mass spectrometry," or "MS/MS." MS/MS methods are useful for the analysis of complex mixtures, especially biological samples, in part because the selectivity of MS/MS can minimize the need for extensive sample clean-up prior to analysis.

In an embodiment, the methods and systems of the present disclosure use a triple quadrupole MS/MS (see e.g., Yost, Enke in Ch. 8 of Tandem Mass Spectrometry, Ed. McLafferty, pub. John Wiley and Sons, 1983). Triple quadrupole MS/MS instruments typically consist of two quadrupole mass filters separated by a fragmentation means. In one embodiment, the instrument may comprise a quadrupole mass filter operated in the RF only mode as an ion containment or transmission device. In an embodiment, the quadropole may further comprise a collision gas at a pressure of between 1 and 10 millitorr. Many other types of "hybrid" tandem mass spectrometers are also known, and can be used in the methods and systems of the present disclosure including various combinations of magnetic sector analyzers and quadrupole filters. These hybrid instruments often comprise high resolution magnetic sector analyzers (i.e., analyzers comprising both magnetic and electrostatic sectors arranged in a double-focusing combination) as either or both of the mass filters. Use of high resolution mass filters may be highly effective in reducing chemical noise to very low levels.

For the methods and systems of the present disclosure, ions can be produced using a variety of methods including, but not limited to, electron ionization, chemical ionization, fast atom bombardment, field desorption, and matrix-assisted laser desorption ionization ("MALDI"), surface enhanced laser desorption ionization ("SELDI"), photon ionization, electrospray ionization, and inductively coupled plasma.

A plurality of analytes can be analyzed simultaneously or sequentially by the presently disclosed LC-MS/MS and 2D-LC-MS/MS methods. Exemplary analytes amenable to analysis by the presently disclosed methods include, but are not limited to, vitamins, such as ascorbic acid. One of ordinary skill in the art would recognize after a review of the presently disclosed subject matter that other similar analytes could be analyzed by the methods and systems disclosed herein. Thus, in alternate embodiments, the methods and systems may be used to quantify vitamins, peptide and protein biomarkers, drugs of abuse and therapeutic drugs. For example, optimization of key parameters for each analyte can be performed using a modular method development strategy to provide highly tuned bioanalytical assays. Thus, certain steps may be varied depending upon the analyte being measured as disclosed herein.

Also, embodiments of the methods and systems of the present disclosure may provide greater sensitivity than the sensitivities previously attainable for many of the analytes being measured. For example, through using this optimization procedure, an LOQ of about 0.05 milligram per deciliter (mg/dL), or less than 0.1 mg/dL, or less than 1 mg/dL, or less than 5 mg/dL is attained for the analysis of ascorbic acid. The levels of detection may allow for the analysis of sample volumes ranging from 0.5 mL to greater than 1 mL.

Embodiments of the present disclosure may provide certain advantages. In certain embodiments, the methods and systems of the present disclosure may provide greater sensitivity than the sensitivities previously attainable for many of the analytes being measured.

Also, embodiments of the methods and systems of the present disclosure may provide for rapid throughput that has previously not been attainable for many of the analytes being measured. For example, using the methods and systems of the present disclosure, multiple samples may be analyzed for ascorbic acid using 96 well plates and a multiplex system of four LC-MS/MS systems, significantly increasing the throughput.

As another advantage, the specificity and sensitivity provided by the methods and systems of the present disclosure may allow for the analysis of analytes from a variety of biological materials. For example, the 2D-LC-MS/MS methods of the present disclosure can be applied to the quantification of analytes of interest in complex sample biological matrices, including, but not limited to, blood, serum, plasma, urine, saliva, and the like. Thus, the methods and systems of the present disclosure are suitable for clinical applications and/or clinical trials.

As additional potential advantages, in certain embodiments, the systems and methods of the present disclosure provide approaches for addressing isobaric interferences, varied sample content, including hemolysed and lipemic samples, while attaining low mg/dL limits of quantification (LOQ) of the target analytes. Accordingly, embodiments of the methods and systems of the present disclosure may provide for the quantitative, sensitive, and specific detection of clinical biomarkers used in the clinical diagnosis of disorders.

Validation of LC-MS MS Assays for Ascorbic Acid

Specificity of the assay in calibrator matrix was assessed by evaluating the interference among the matrices for ascorbic acid and $^{13}C_6$-ascorbic acid. No interference was observed in calibrator matrix (1% (w/v) BSA, 100 mM Tris-acetate, pH 6.0, 1% (w/v) sodium metabisulfite and the assay specificity for ascorbic acid was unaffected by $^{13}C_6$-ascorbic acid. Further, carryover in three double blanks following 2× the ULOQ is less than that observed in the LLOQ. These results indicate the assay is specific for the analysis of ascorbic acid in calibrator matrix.

Given the specificity of the assay, the accuracy and precision of the calibrators and quality controls was evaluated across intra-assay (20×1) and inter-assay (5×5 or 1×20) studies. The results indicated the assay was accurate and precise for the measurement of ascorbic acid. Finally, calibrator reproducibility was shown across 5 separate analytical runs.

The relative accuracy of the assay for ascorbic acid spiked into calibrator matrix and lithium-heparin plasma was next evaluated by performing mixing and spike and recovery studies. Accurate ascorbic acid measurements after mixing of a high-level calibrator and lithium-heparin plasma at 3:1, 1:1, and 1:3 ratios indicate matrix equivalency. Spike and recovery demonstrates the assay recovery of ascorbic acid at 4, 20, and 80× the LLOQ in three lithium-heparin plasma specimens. These results indicate the assay is accurate in carrier matrix and lithium-heparin plasma.

The specificity and accuracy of the ascorbic acid measurement was interrogated in the presence of interferents. Only 300 mg/dL triglycerides from the Assurance Test Kit affects the analytical measurement of ascorbic acid, whereas 500 mg/dL hemoglobin, 20 mg/dL conjugated or unconjugated bilirubin, and 12 mg/dL total protein does not. Given that the acceptable concentration of triglycerides using the assurance test kit is 300 mg/dL, which is in the borderline-high region, a sample mixing experiment was performed to adjudicate acceptable triglyceride levels. Two lipemic pools from serum samples were created and triglyceride levels measured using a Cobas 8000 instrument. Sample mixing was performed using the high matrix control (QC3) to determine accuracy of quantification in the intended sample type. Gross lipemia (up to 2080.8 mg/dL) did not affect the accuracy of ascorbic acid measurement as demonstrated by sample mixing with a normal serum pool. The measurement of ascorbic acid was not affected by myriad exogenous hormones or drug and organic acid cocktails. Thus, the assay is accurate in the presence of interferents.

Assay accuracy was evaluated when samples are diluted before extraction or after extraction. Results from these studies demonstrate specimens can be diluted up to 10-fold before extraction using calibrator matrix or can be diluted after extraction using 1:4 10% TCA:acetonitrile up to 50-fold. These studies indicate that patients yielding ascorbic acid values above the ULOQ (5 mg/dL) can be diluted into range before extraction using calibrator matrix or after extraction using 1:4 10% TCA:acetonitrile, or a combination of both.

Three high-level samples were evaluated for dilutional linearity. Linearity was evaluated by diluting the samples 2- and 10-fold using blank matrix (1% (w/v) BSA, 0.1% (w/v) sodium metabisulfite, Tris-acetate, pH 6.0). Mean result in one diluted sample using water was ≥±15% bias relative to the mean result observed in the corresponding neat sample. However, mean result in each diluted sample using blank matrix was ≤±15% bias relative to the mean result observed in the corresponding neat sample. These results indicate high-level samples may be diluted 2- or 10-fold using blank matrix prior to extraction.

The stability of samples was interrogated. First, calibrator, quality control, and specimen stability was interrogated at room temperature (15-30° C.), refrigerated (2-8° C.), and frozen (<−10° C.), frozen (<−70° C.) and through freeze-thaw cycles. The calibrators are stable for 2 hours room temperature, 4 hours refrigerated, 24 hours frozen (<−10° C.), and 33 days frozen (<−70° C.). The calibrators are stable through one freeze-thaw cycle. The QCs are also stable for 2 hours at RT, 4 hours refrigerated, 24 hours frozen (−20° C.), and 32 days frozen (<−70° C.). In contrast to the calibrators, QCs are stable through two freeze-thaw cycles.

To evaluate recovery, blank calibrator matrix was spiked with ascorbic acid to levels at approximately 4 (+0.2 mg/dL), 20 (+1 mg/dL) and 80 (+4 mg/dL) times the assay LLOQ. Three lithium-heparin patients were drawn in-house, processed according to our protocol, and spiked in a similar fashion to the blank calibrator matrix. Spiked and un-spiked samples were assayed in quadruplicate. Recovery in each spiked sample was calculated as the mean measurement from the spiked sample divided by the sum of (1) the mean measurement from the un-spiked sample and (2) the nominal spiked amount, expressed as a percentage. The nominal spiked amount was determined by the mean of at least four replicate measurements of blank calibrator matrix spiked in an identical manner and assayed in parallel with the spiked and un-spiked sample. The recovery determined at each concentration fell between 85 and 115% of the expected mixed concentration. These results suggest that the measurement of ascorbic acid is accurate in lithium-heparin plasma.

Illustrative Embodiments of Suitable Methods and Systems

As used below, any reference to methods or systems is understood as a reference to each of those methods or systems disjunctively (e.g., "Illustrative embodiment 1-4 is understood as illustrative embodiment 1, 2, 3, or 4.").

Illustrative embodiment 1 is a method for determining the presence or amount of ascorbic acid in a sample by tandem mass spectrometry, comprising: (a) generating a fragment ion from the ascorbic acid of with a mass to charge ratio (m/z) of about 115 by in-source fragmentation; (b) generating one or more product ions of the ascorbic acid fragment ion by tandem mass spectrometry and (c) detecting the presence or amount of one or more of the ascorbic acid fragment ion generated in step (a) or the one or more product ions of step (b) or both, and relating the detected ions to the presence or amount of the ascorbic acid in the sample.

Illustrative embodiment 2 is the method of any preceding or subsequent illustrative embodiment, wherein the sample is subjected to a purification step prior to the initial fragmentation step (a).

Illustrative embodiment 3 is the method of any preceding or subsequent illustrative embodiment, wherein the purification step comprises chromatography and/or precipitation of proteins.

Illustrative embodiment 4 is the method of any preceding or subsequent illustrative embodiment, wherein the chromatography comprises high performance liquid chromatography (HPLC).

Illustrative embodiment 5 is the method of any preceding or subsequent illustrative embodiment, wherein the chromatography comprises analytical liquid chromatography.

Illustrative embodiment 6 is the method of any preceding or subsequent illustrative embodiment, wherein the sample is heated at the MS/MS interface.

Illustrative embodiment 7 is the method of any preceding or subsequent illustrative embodiment, further comprising at least one of liquid-liquid extraction of the sample or dilution of the sample prior to mass spectrometry.

Illustrative embodiment 8 is the method of any preceding or subsequent illustrative embodiment, wherein the product ions comprise ions having a mass/charge ratio (m/z) of about 87 and 59.

Illustrative embodiment 9 is the method of any preceding or subsequent illustrative embodiment, wherein the fragment ion comprises 3,4-dihyroxyfuran-2 (5H)-one.

Illustrative embodiment 10 is the method of any preceding or subsequent illustrative embodiment, wherein the product ions comprise at least one of (Z)-prop-1-ene-1,2,3-triol diradical or (Z)-ethene-1,2-diol radical.

Illustrative embodiment 11 is the method of any preceding or subsequent illustrative embodiment, further comprising detection of ascorbic acid over a range of from about 0.05 mg/dL to about 5 mg/dL.

Illustrative embodiment 12 is the method of any preceding or subsequent illustrative embodiment, further comprising providing a biological sample believed to contain ascorbic acid.

Illustrative embodiment 13 is the method of any preceding illustrative embodiment, wherein the tandem MS/MS spectrometer is operated in an atmospheric pressure chemical ionization (APCI) mode.

Illustrative embodiment 14 is a system for determining the presence or amount of ascorbic acid in a test sample, the system comprising: a station for providing a test sample suspected of containing ascorbic acid; optionally, a station for partially purifying the ascorbic acid from other components in the sample; optionally, a station for chromatographically separating the ascorbic acid from other components in the sample; a station for in-source fragmentation of the ascorbic acid to generate an ascorbic acid fragment ion; and a station for mass spectrometry to generate product ions from the ascorbic acid fragment ion; and a station to analyze the mass spectrum to determine the presence or amount of ascorbic acid in the test sample.

Illustrative embodiment 15 is the system of any preceding or subsequent illustrative embodiment, further comprising a station for partially purifying the ascorbic acid from other components in the sample.

Illustrative embodiment 16 is the system of any preceding or subsequent illustrative embodiment, further comprising a station for chromatographically separating the ascorbic acid from other components in the sample Illustrative embodiment 17 is the system of any preceding illustrative embodiment, wherein at least one of the stations is controlled by a computer.

Illustrative embodiment 18 is a method for determining the presence or amount of ascorbic acid in a biological sample, the method comprising: providing a biological sample believed to contain ascorbic acid; chromatographically separating the ascorbic acid from other components in the sample; generating a fragment ion of the ascorbic acid; applying the ascorbic acid fragment ion to a mass spectrometer to generate product ions; and analyzing the ascorbic acid fragment ion and/or product ions by mass spectrometry to determine the presence or amount of ascorbic acid in the sample.

Illustrative embodiment 19 is the method of any preceding or subsequent illustrative embodiment, further comprising partially purifying the ascorbic acid by protein precipitation prior to chromatography.

Illustrative embodiment 20 is the method of any preceding or subsequent illustrative embodiment, wherein the ascorbic acid fragment ion is made by in-source fragmentation.

Illustrative embodiment 21 is the method of any preceding or subsequent illustrative embodiment, wherein the product ions comprise ions having a mass/charge ratio (m/z) of about 87 and 59.

Illustrative embodiment 22 is the method of any preceding or subsequent illustrative embodiment, further comprising detection of ascorbic acid over a range of from about 0.05 mg/dL to about 5 mg/dL.

Illustrative embodiment 23 is the method of any preceding or subsequent illustrative embodiment, wherein the biological sample comprises blood, serum, plasma, urine, or saliva.

Illustrative embodiment 24 is the method of any preceding or subsequent illustrative embodiment, wherein the chromatography comprises high performance liquid chromatography (HPLC).

Illustrative embodiment 25 is the method of any preceding or subsequent illustrative embodiment, wherein the chromatography comprises analytical liquid chromatography.

Illustrative embodiment 26 is the method of any preceding or subsequent illustrative embodiment, wherein the partial purification comprises liquid-liquid extraction.

Illustrative embodiment 27 is the method of any preceding illustrative embodiment, further comprising diluting the sample into a solvent used for liquid chromatography or mass spectrometry.

Various embodiments of the disclosure have been described herein. It should be recognized that these embodiments are merely illustrative of the present disclosure. Variations of those preferred embodiments may become apparent to those of ordinary skill in the art upon reading the foregoing description. It is expected that skilled artisans can employ such variations as appropriate, and the disclosure is intended to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated or otherwise clearly contradicted by context.

What is claimed is:

1. A method for determining an amount of ascorbic acid in a biological sample by tandem mass spectrometry, comprising:

(a) generating a precursor fragment ion from ascorbic acid having a mass to charge ratio (m/z) of about 115 by in-source fragmentation prior to entry of the precursor fragment ion into a quadrupole of a tandem mass spectrometer;

(b) generating a product ion of the precursor fragment ion by tandem mass spectrometry (MS/MS), wherein the product ion has a mass/charge ratio (m/z) of about 59;

(c) detecting the amount of the product ion generated in (b); and (d) relating the detected product ion to the amount of the ascorbic acid in the biological sample.

2. The method of claim 1, wherein the biological sample is subjected to a purification step prior to the initial fragmentation step (a).

3. The method of claim 2, wherein the purification step comprises chromatography and/or precipitation of proteins.

4. The method of claim 3, wherein the chromatography comprises high performance liquid chromatography (HPLC).

5. The method of claim 3, wherein the chromatography comprises analytical liquid chromatography.

6. The method of claim 4, wherein the biological sample is heated at an MS/MS interface.

7. The method of claim 1, further comprising subjecting the biological sample to liquid-liquid extraction or diluting the biological sample prior to (a).

8. The method of claim 1, further comprising generating a second product ion of the precursor fragment ion by tandem mass spectrometry (MS/MS), wherein the second product ion has a mass/charge ratio (m/z) of about 87, detecting the amount of the second product ion, and relating the detected second product ion to the amount of the ascorbic acid in the biological sample.

9. The method of claim 1, wherein the precursor fragment ion comprises 3,4-dihydroxyfuran-2 (5H)-one.

10. The method of claim 1, wherein the product ion comprises (Z)-ethene-1,2-diol radical.

11. The method of claim 1, wherein the lower limit of quantification (LLOQ) of ascorbic acid is 0.05 mg/dL.

12. The method of claim 1, further comprising, prior to (a), providing a biological sample believed to contain the ascorbic acid and wherein (a) further comprises applying a voltage to an orifice plate.

13. The method of claim 1, wherein the tandem MS/MS spectrometer is operated in an atmospheric pressure chemical ionization (APCI) mode.

14. The method of claim 8, wherein the second product ion comprises (Z)-prop-1-ene-1,2,3-triol diradical.

* * * * *